United States Patent [19]

Baldwin et al.

[11] Patent Number: 4,803,286

[45] Date of Patent: Feb. 7, 1989

[54] AMINO-2-HYDROXYPROPYLOX-IMINOHETEROCYCLE α-BLOCKERS

[75] Inventors: John J. Baldwin, Gwynedd Valley; Gerald S. Ponticello, Lansdale; David C. Remy, North Wales; David A. Claremon, Audubon; Stella W. King, Lansdale, all of Pa.

[73] Assignee: Merck & Co., Inc., Rahway, N.J.

[21] Appl. No.: 87,124

[22] Filed: Aug. 19, 1987

[51] Int. Cl.$^4$ .................. C07D 335/02; A61K 31/38; A61K 31/385

[52] U.S. Cl. ..................... 514/431; 514/432; 514/447; 514/443; 514/439; 514/640; 549/28; 549/68; 549/11; 549/23; 549/50; 549/57; 549/38; 549/21; 549/9; 564/256

[58] Field of Search ............ 549/68, 28, 11, 38, 549/21, 9; 514/431, 432, 433, 439, 447

[56] References Cited

PUBLICATIONS

Sanufi, CA 95:150421p.
Seth et al., CA 100:6246q.
Baldwin et al., J. Med. Chem., 1982, 25,931.
Bouzoubba et al., J. Med. Chem., 1984, 27,1291–1294.
Granados et al., Anales De Quimica, 1983, 79,275–282.
Fravolini et al., Eur. J. Med. Chem., 1978, 13, 347–350.

Primary Examiner—Jane T. Fan
Attorney, Agent, or Firm—William H. Nicholson; Michael C. Sudol, Jr.

[57] ABSTRACT

Certain amino-2-hydroxypropyloximinoheterocycles are β-adrenoceptor antagonists useful in the treatment of elevated intraocular pressure, hypertension, angina and arrhythmia.

7 Claims, No Drawings

AMINO-2-HYDROXYPROPYLOX-IMINOHETEROCYCLE α-BLOCKERS

SUMMARY OF THE INVENTION

This invention is concerned with a compound of structural formula I:

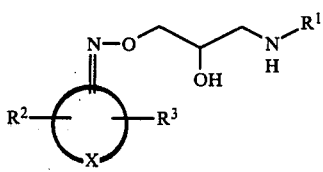

or a pharmacologically acceptable salt thereof, wherein X, $R^1$, $R^2$, and $R^3$, are as hereinafter defined.

It is also concerned with a method of treating elevated intraocular pressure and the disease states associated therewith, such as glaucoma, by topical ocular administration of a compound of structural formula I, and the treatment of hypertension, angina and arrhythmia by oral, parenteral or rectal administration.

The invention is also concerned with pharmaceutical formulations of a compound of structural formula I, and processes for preparing such compounds.

BACKGROUND OF THE INVENTION

Glaucoma is an ocular disorder associated with elevated ocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that a few β-adrenergic blocking agents are effective in reducing intraocular pressure. While many of these agents are effective in reducing intraocular pressure, they also have other characteristics, e.g. local anesthetic activity, that are not acceptable for chronic ocular use.

(S)-1-tert-butylamino-3-[(4-morpholino-1,2,5-thiadiazol-3-yl)oxy]-2-propanol, a β-adrenergic blocking agent, was found to reduce intraocular pressure and to be devoid of many unwanted side effects associated with pilocarpine and, in addition, to possess advantages over many other β-adrenergic blocking agents, e.g. to be devoid of local anesthetic properties, to have a long duration of activity, and to display minimal tolerance.

β-Adrenergic antagonists of the oxime type are known in the literature. Amino-2-hydroxypropyloximinofluorenes are described by Inibs et al, *Br. J. Pharmacol.*, 60, 357 (1977) and Baldwin et al, *J. Med. Chem.*, 25, 931 (1982); oxime ether derivatives of certain aromatic carboxaldehydes are described by Granados et al., *Anales De Quimica*, 79, 275 (1983); Oxime ether derivatives of thiochroman-4-ones are described by Fravolini et al., *Eur. J. Med. Chem.*, 13, 347 (1978); and aliphatic and alicyclic oxime ethers are described by Baazoubba et al, *J. Med. Chem.*, 27, 1291 (1984); 28, 896 (1985).

However, known β-adrenergic blocking agents have not been shown to demonstrate any meaningful oculoselectivity and, in spite of the low dose normally required for ocular administration, manifest their β-blocking properties in extra-ocular tissue, especially the pulmonary and cardiovascular systems to such an extent that they should not be administered to patients with pulmonary or cardiovascular ailments.

Now, with the present invention there are provided compounds, with β-blocking properties some of which are particularly useful for topical optical administration for the treatment of ocular hypertension; pharmaceutical formulations of those compounds; methods of treating ocular hypertension, hypertension, angina and arrhythmia with those compounds and processes for preparation of those compounds.

DETAILED DESCRIPTION OF THE INVENTION

One embodiment of this invention is the novel compound of structural formula I:

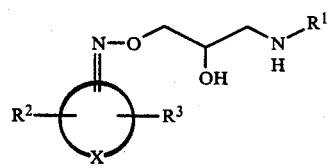

or a pharmacologically acceptable salt thereof wherein
X is —S—, —CH=CH—, or —S(CH$_2$)$_2$S—;
$R^1$ is C$_{1-6}$ alkyl, or phenyl-C$_{1-6}$alkyl;
$R^2$ and $R^3$ are independently
  (a) hydrogen,
  (b) C$_{1-6}$ alkyl, either unsubstituted or substituted with —OH, —COR$^1$ or COAr or OCOR$^1$,
  (c) —COOR$^1$; or
$R^2$ and $R^3$ can be joined together to form a thiophene ring; and

represents a non-aromatic, monocyclic ring of from 5 to 8 members such as tetrahydrothiopyran, cycloheptene, thiepane, 1,4-dithiepane or tetrahydrothiophene.

The term "alkyl" is meant to include straight chain alkyl, branched chain alkyl, cycloalkyl, cycloalkyl-alkyl, alkyl-cycloalkyl-alkyl and alkyl-cycloalkyl.

The term "Ar" means aryl and includes carbocyclic aryl such as phenyl and naphthyl, and heterocyclic aryl such as pyridyl, thienyl, furyl or the like.

The compounds found particularly useful for treatment of ocular hypertension are those wherein $R^1$ is t-butyl or isopropyl;

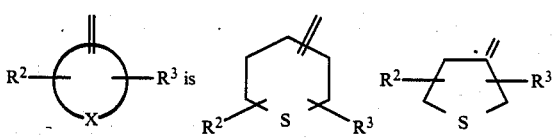

-continued

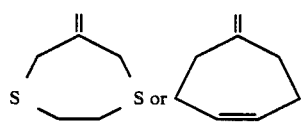

wherein $R^2$ and $R^3$ are independently hydrogen or $C_{1-2}$alkyl either unsubstituted or substituted with —$OCH_3$, or —$OCOCH_3$.

Important species within the ophthalmic group have structural formula:

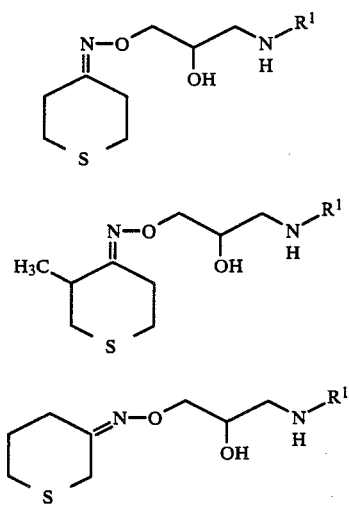

wherein $R^1$ is t-butyl or isopropyl.

The pharmacologically acceptable salts of the compounds of this invention include those prepared from inorganic acids such as hydrochloric, and those formed from organic acids such as maleic acid, citric acid, pamoic acid, pyruvic acid, fumaric acid, oxalic acid, tartaric acid or the like.

All of the novel compounds of this invention are propan-2-ol-3-amines in which the 2-carbon carrying the hydroxyl group is asymmetric giving rise to (R)- and (S)-enantiomers with respect to that asymmetric center. Either enantiomer or mixtures of the (S)- and (R)-enantiomers such as the racemic mixtures form a part of this invention.

The introduction of nuclear substituents, $R^2$ and/or $R^3$, into I results in the formation of new centers of asymmetry, which, together with the asymmetric center described previously, leads to the formation of diastereomeric mixtures. Further, the introduction of substituents $R^1$, $R^2$ and $R^3$ that are themselves capable of optical isomerism, also leads to the formation of diastereomeric mixtures. This invention includes all of the possible isomers and all of the possible mixtures of isomers contributed by $R_1$, $R_2$, $R_3$ and the 2-hydroxy group.

Furthermore, the oximino function may exist in the (E)- or (Z)-configuration and this invention also includes these isomers and mixtures thereof.

A second embodiment of this invention is the novel process for preparing the above described novel compounds. It is exemplified by the following reaction scheme:

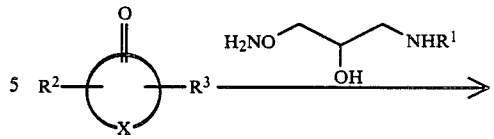

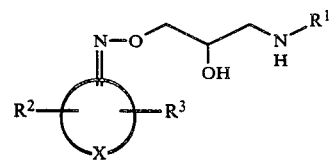

The two reagents, with a slight excess of the hydroxylamine ether, and about 2 moles of sodium acetate per mole of hydroxylamine ether in aqueous $C_{1-3}$alkanol, preferably ethanol are heated at about 75° C. to reflux temperature for about 1 to 5 hours. After cooling and neutralization, the product is isolated by extraction with an organic solvent.

Another novel process for preparing the compounds of this invention is illustrated as follows:

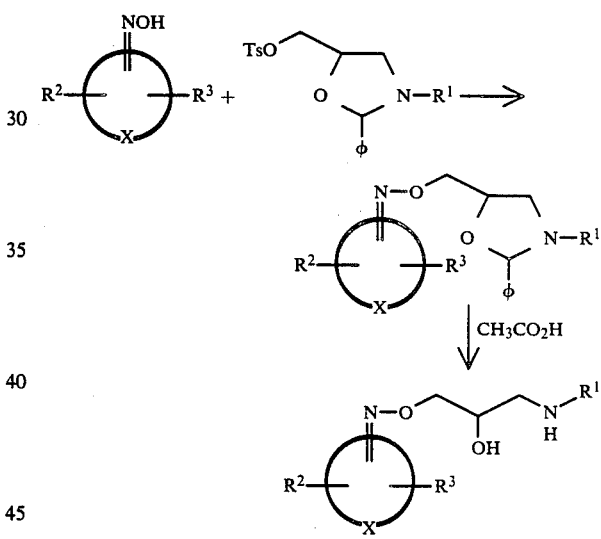

A mixture of the oxime, and a strong base such as sodium hydride in a solvent such as DMF is heated to about 40°–70° C. and then treated dropwise with a DMF solution of 2-phenyl-3-$R^1$-5-toluenesulfonyloxymethyloxazolidine. After about 12 to 24 hours at about 75° to 120° C., the mixture is poured into water, extracted with an organic solvent and concentrated to dryness. The residue is then agitated with acetic or similar acid at about 15° to 25° C., preferably room temperature for about 12 to 24 hours to open the oxazolidine ring.

A third embodiment of this invention is the method of treating elevated intraocular pressure by the topical ocular administration to a patient in need of such treatment of an effective intraocular pressure lowering amount of a compound of formula I or an ophthalmologically acceptable salt thereof.

A unit dose comprises about 0.001 to 5.0 mg, preferably about 0.005 to 2.0 mg, and especially about 0.05 to 1.0 mg of active compound per eye. Multiple unit doses are administered as needed to achieve and maintain a normotensive or close to normotensive ocular condition.

A fourth embodiment of this invention is the novel ophthalmic formulation comprising one of the novel compounds as active ingredient. The ophthalmic composition of this invention may be in the form of a solution, suspension, ointment, gel or solid insert and contains about.0.01 to 5% and especially about 0.5 to 2% by weight of medicament. Higher concentrations as, for example, about 10% or lower concentrations can be employed. The active compound in the formulation or method of treatment may be employed as the sole active ingredient or in combination with other β-blockers, such as timolol maleate; a parasympathomimetic agent such as pilocarpine, or a topically effective carbonic anhydrase inhibitor. The agents would be employed in approximately equal amounts.

The β-adrenergic blocking properties of the novel compounds of this invention indicate that they are also useful in the treatment of conditions such as hypertension, angina pectoris, or certain arrhythmias which are known to be amenable to treatment with β-adrenergic blocking agents.

For use as extra-ocular β-adrenergic blocking agents, the present compounds can be administered orally, transdermally, or parenterally; i.e., intravenously, interperitoneally, etc. and in any suitable dosage form. The compounds may be offered in a form (a) for oral administration; e.g., as tablets, in combination with other compounding ingredients customarily used such as talc, vegetable oils, polyols, benzyl alcohols, gums, gelatin, starches, and other carriers; as liquids dissolved or dispersed or emulsified in a suitable liquid carrier; in capsules encapsulated in a suitable encapsulating material; or (b) for parenteral administration dissolved or dispersed in a suitable liquid carrier such as solution or as an emulsion, or (c) as an aerosol or patch for transdermal administration. The ratio of active compound to compounding ingredients; i.e., carrier, diluent, etc., will vary as the dosage form requires. Generally, doses of the present compounds of from about 0.01 to about 50 mg/kg and preferably from about 0.1 to about 20 mg/kg of body weight per day may be used. Dosage may be single or multiple depending on the daily total required and the unit dosage.

EXAMPLE 1

Tetrahydro-4H-thiopyran-4-one-0-(3-((1,1-dimethylethyl)amino)-2-hydroxypropyl)oxime monohydrochloride To a solution of tetrahydrothiopyran-4-one (1.0 g, 8.6 mmol) in ethanol (29 ml) was added a solution of 3-t-butylamino-2-hydroxypropoxyamine dihydrochloride (2.4 g, 10.3 mmol) in 2:1 water-ethanol (3.8 ml). Sodium acetate trihydrate (2.8 g, 20.6 mmol) in 2:1 water-ethanol (7.6 ml) was added and the mixture was refluxed for 2.5 hours. The solution was concentrated, saturated NaHCO₃ solution added and extracted with ethyl acetate. Drying and solvent evaporation gave an oil (1.8 g). Column chromatography (silica gel, 100% CHCl₃—NH₃) gave the free base (1.1 g). Salt formation was afforded with ethanolic HCl to yield the title compound (0.8 g, 31%), m.p. 130°–132° C.

Employing the procedures substantially as described in Example 1, but substituting the appropriate cyclic oxo compound for tetrahydrothiopyran-4-one and using the appropriate oxime ether, there were produced the oximino compounds identified in Table I:

TABLE I

| Ring | R¹ | m.p. (°C.) | Salt |
|---|---|---|---|
| tetrahydrothiopyran (S) | isopropyl | 115–116 | HCl |
| tetrahydrothiophene (S) | isopropyl | 59–61 | — |
| tetrahydrothiopyran-S,S-dioxide (SO₂) | isopropyl | 156–158 | HCl |
| methyl-tetrahydrothiopyran (CH₃, S) | isopropyl | 80–84 | HCl |
| methyl-tetrahydrothiopyran (CH₃, S) | t-butyl | 118–120 | HCl |
| dithiepane (S, S) | isopropyl | 96–98 | maleate |
| cycloheptenone | isopropyl | 98–104 | 0.5 oxalate·H₂O |

EXAMPLE 2

3-((Acetyloxy)methyl)tetrahydro-4H-thiopyran-4-one-0-(2-hydroxy-3-((1-methylethyl)amino)propyl)oxime, ethanedioate (1:1 salt)

Step A: Preparation of Methyl[spiro-(1-dioxolan-4-tetrahydrothiopyran)-3-yl]carboxylate A mixture of 10.0 g (0.0574 mol) of 3-carbomethoxytetrahydrothiopyran-4-one, 17.8 g (0.287 mol) of ethylene glycol, 50 mg of p-toluenesulfonic acid and 200 ml of benzene were refluxed under a Dean and Stark water separator for 18 hours. The cooled solution was washed with water, a saturated solution of sodium bicarbonate, and was dried over magnesium sulfate. Filtration and evaporation of the solvent gave 12.33 g (98%) of the product ketal-ester.

Step B: Preparation of Spiro-[1'-dioxolan-4-(3-hydroxymethyltetrahydrothiopyran)]

A solution of 10.0 g (0.0458 mol) of product from Step A in 50 ml of ether was added dropwise to a stirred mixture of 1.75 g (0.0458 mol) of lithium aluminum hydride in 50 ml of ether. After the addition was complete, the mixture was stirred at room temperature overnight. A saturated solution of ammonium chloride was added dropwise until a clear ether phase separated from a granular inorganic phase. The ether layer was decanted and the residue was washed well with three additional portions of ether. Evaporation of the combined ether extracts gave 10.09 g of product as a clear oil which showed no carbonyl absorption band in the infrared spectrum, but did show a band at 3410 cm$^{-1}$ (OH).

Step C: Preparation of 3-Hydroxymethyltetrahydrothiopyran-4-one

A solution of 10.0 g of product from Step B in a mixture of glacial acetic acid, water, and THF (3:2:2) was heated at 70° C. for 16 hours. The bulk of the solvent was removed under reduced pressure. A white solid was removed by filtration, and the filtrate was made basic by the addition of solid potassium carbonate. This basified solution was extracted with three 50 ml portions of ether, and the combined ether fractions were washed with water, ddried (MgSO$_4$), filtered, and evaporated to afford 6.70 g (72%) of the title compound.

Step D: Preparation of 3-Acetoxymethyltetrahydrothiopyran-4-one

To an ice-cooled solution of 1.26 g (0.0086 mol) of product from Step C and 1.44 g (0.0142 mol) of triethylamine in 25 ml of methylene chloride was added dropwise 0.75 g (0.0095 mol) of acetyl chloride. The solution was stirred for four hours at 0° C., after which time it was washed with water, a saturated solution of sodium bicarbonate, and water. The organic phase was dried (MgSO$_4$), filtered, and evaporated to give 1.52 g (94%) of product.

Step E: 3-((Acetyloxy)methyl)tetrahydro-4H-thiopyran-4-one-O-(2-hydroxy-3-((1-methylethyl)amino)propyl)oxime, ethanedioate (1:1 salt)

A solution of 1.52 g (0.00807 mol) of product from Step D, 2.14 g (0.0097 mol) of O-(3-isopropylamino-2-hydroxypropyl hydroxylamine dihydrochloride, 2.64 g (0.01938 mol) of sodium acetate trihydrate, 35 ml of absolute ethanol, and 10 ml of water was stirred and refluxed for 6 hours. The bulk of the solvent was removed under reduced pressure and the residue was made basic with a saturated solution of NaHCO$_3$. After adding some solid sodium chloride, the mixture was extracted with three 50 ml portions of ethyl acetate. The extracts were combined, dried (MgSO$_4$), filtered, and evaporated. The product was isolated and purified by flash chromatography on silica gel using 2.5% methanol in chloroform saturated with NH$_3$ (g) to give 1.0 g of product as a clear, colorless, chromatographically homogeneous oil. An oxalate salt was prepared and crystallized from isopropyl alcohol m.p. 146°–156° C.

Anal. Calc'd for C$_{14}$H$_{26}$N$_2$O$_4$S.C$_2$H$_2$O$_4$: C, 47.04; H, 6.91; N, 6.86. Found: C, 46.87; H, 7.07; N, 7.03.

EXAMPLE 3

Tetrahydro-3-(hydroxymethyl)-4H-thiopyran-4-one-O-(2-hydroxy-3-((1-methylethyl)amino)propyl)oxime, ethanedioate (1:1 salt)

A mixture of 1.5 g of product from Example 2, 50 ml of methanol, 5 ml of 10% aqueous sodium hydroxide solution, and 15 ml of water, was stirred overnight at room temperature. The bulk of the ethanol was removed under reduced pressure, and the residual aqueous mixture was saturated with solid potassium carbonate. This mixture was extracted twice with 100 ml portions of ether, and the combined ether extracts were dried, filtered, and evaporated to give 1.21 g of a clear oil. Chromatography of this oil on a flash silica gel column using 3% methanol in chloroform saturated with gaseous ammonia afforded 0.357 g of recovered ester starting material, and 0.705 g of the desired alcohol product. The hydrogen oxalate salt was prepared and crystallized from isopropyl alcohol-ether; m.p. 95°–105° C.

Anal. Calc'd for C$_{12}$H$_{24}$N$_2$O$_3$S.C$_2$H$_2$O$_4$: C, 45.89; H, 7.15; N, 7.65. Found: C, 45.75; H, 7.37; N, 7.87.

EXAMPLE 4

Methyl tetrahydro-4-((2-hydroxy-3-((1-methylethyl)amino)-propoxy)imino-2H-thiopyran-3-carboxylate, ethanedioate (1:1 salt)

Reaction of 3-carbomethoxy-thiopyran-4-one (1.50 g, 0.00861 mol) with 2.28 g (0.0103 mol) of O-(3-isopropylamino-2-hydroxypropyl)hydroxylamine dihydrochloride and 2.80 g (0.0207 mol) of sodium acetate trihydrate in a mixture of 35 ml of methanol and 10 ml of water at reflux for 8 hours afforded the title compound. The hydrogen oxalate salt was prepared and crystallized from isopropyl alcohol-ether; m.p. 75°–80° C.

Anal. Calc'd for C$_{13}$H$_{24}$N$_2$O$_4$S.C$_2$H$_2$O$_4$: C, 45.67; H, 6.65; N, 7.10. Found: C, 45.42; H, 6.63; N, 7.38.

EXAMPLE 5

Tetrahydro-2-methyl-4H-thiopyran-4-one-O-(2-hydroxy-3-((1-methylethyl)aminopropyl)oxime, (Z)-2-butanedioate (1:1 salt)

Step A: Preparation of 1,4-dioxa-7-methyl-8-thiaspiro[4,5]decane

To a solution of 0.97 g (5.0 mmol) of 7-chloro-1,4-dioxa-8-thiaspiro[4,5]decane in 20 ml of dry ether cooled in a dry ice-acetone bath was added 5.9 mmol of methyl magnesium bromide solution in ether. The resulting mixture was stirred for 18 hours while warming to room temperature. Saturated ammonium chloride solution (5 ml) was added, the mixture was diluted with 5 ml water, and the layers were separated. The aqueous layer was extracted with ether (20 ml). The combined extract was washed with brine, dried over sodium sulfate, filtered, and concentrated in vacuo to give 0.75 g (86%). product as an oil; NMR (deuteriochloroform): δ

4.0 (m, 4H), 3.1 (m, 1H), 2.9 (m, 1H), 2.6 (m, 1H), 2.0 (d of d, 2H), 1.7 (m, 1H), 1.6 (m, 1H), 1.2 (d, 3H).

Step B: Preparation of 4H-2,3,5,6-tetrahydro-2-methylthiopyran-4-one

A solution of 0.63 g (3.6 mmol) of product from Step A, 8 ml of water, 8 ml of tetrahydrofuran, and 12 ml of acetic acid was heated at 80° C. for 18 hours. The mixture was concentrated in vacuo and the residue was dissolved in 50 ml of ether. The ether solution was washed with saturated sodium bicarbonate solution (20 ml), water (20 ml), and brine, dried over sodium sulfate, filtered and concentrated to give 0.35 g (75%) product as an oil; NMR (deuteriochloroform): δ 3.2 (m, 1H), 2.9 (m, 2H), 2.7 (m, 3H), 2.2 (d of d, 1H), 1.3 (d, 3H).

Step C: Tetrahydro-2-methyl-4H-thiopyran-4-one-O-(2-hydroxy-3-((1-methylethyl)aminopropyl)oxime, (Z)-2-butanedioate (1:1 salt)

To a solution of 1.03 g (7.9 mmol) of product from Step B and 2.11 g (9.5 mmol) of 3-(1-methylethylamino)-2-hydroxypropoxyamine dihydrochloride in 32 ml of ethanol and 8 ml of water was added 1.56 g (19.0 mmol) of sodium acetate. The resulting solution was heated at reflux for 2.5 hours, cooled, and concentrated in vacuo. The residue was partitioned between saturated sodium bicarbonate solution (60 ml) and ethylacetate (120 ml). The aqueous layer was extracted with ethyl acetate (120 ml). The combined extract was washed with brine, dried over sodium sulfate, filtered, and concentrated in vacuo to give 1.37 g of an oil. The oil was flash chromatographed on silica gel eluting with chloroform:ammonia (saturated) to give 1.17 g (57%) product as an oil; NMR (deuteriochloroform): δ 4.0 (m, 2H), 3.9 (m, 1H), 3.3 (m, 1H) 3.0 (m, 1H), 2.8 (m, 4H), 2.7 (m, 2H), 2.4 (m, 1H), 2.2 (m, 1H), 2.1 (m, 1H), 1.3 (d of d, 3H), 1.1 (d of d, 6H).

To a solution of 1.12 g (4.3 mmol) of the oil in 3 ml of isopropanol was added a warm solution of 0.50 g (4.3 mmol) of maleic acid in 2 ml of isopropanol. The resulting solution was diluted with ether (20 ml) and cooled. The resulting precipitate was filtered off to give 11.1 g (69%) of the maleate salt; m.p. 79°–85° C.

Anal. Calc'd for $C_{12}H_{24}N_2O_2S \cdot C_4H_4O_4$: C, 51.04; H, 7.50; N, 7.44. Found: C, 51.35; H, 7.61; N, 7.44.

Employing the procedure substantially as described in Example 5, Step C, but starting with the appropriate ketone, there were prepared the following oximino compounds:

Dihydro-2H-thiopyran-3(4H)-one-O-(2-hydroxy-3-((1-methylethyl)amino)propyl)oxime, ethanedioate (1:1 salt, m.p. 150.5°–152.5° C.;

Dihydro-2-methyl-2H-thiopyran-3(4H)-one-O-(2-hydroxy-3-((1-methylethyl)amino)propyl)oxime, ethanedioate (1:1 salt), m.p. 97°–101° C.;

3-Methyl-4-thiepanone-O-(2-hydroxy-3-((1-methylethyl)amino)propyl)oxime, ethanedioate (1:1 salt), m.p. 80.5°–81.5° C.

Dihydro-2-methyl-3(2H)-thiophenone-O-(2-hydroxy-3-((1-methylethyl)amino)propyl)oxime, ethanedioate (2:1 salt), hemihydrate, m.p. 97°–101° C.;

4-Thiepanone-O-(2-hydroxy-3-((1-methylethyl)amino)propyl)oxime, (Z)-2-butenedioate (1:1 salt), m.p. 80.5°–81.5° C.

EXAMPLE 6

Tetrahydro-3-(2-methoxyethyl)-4H-thiopyran-4-one-O-(2-hydroxy-3-((1-methylethyl)amino)propyl)oxime, ethanedioate (1:1 salt)

Step A: Preparation of 4H-2,3,5,6-tetrahydro-3-carbomethoxy-3-(2-methoxy)ethylthiopyran-4-one To a solution of 5.3 g (25 mmol) of potassium enolate of 4H-2,3,5,6-tetrahydro-3-carbomethoxythiopyran-4-one in 50 ml DMSO, was added 3.47 g (25 mmol) of 2-bromoethyl methyl ether. The solution was stirred under $N_2$ at room temperature for 4 days. The reaction mixture was poured into 500 ml $H_2O$ and extracted three times with ethyl acetate. The combined ethyl acetate solution was washed with water; 5% NaOH; $H_2O$ and brine; dried over magnesium sulfate, filtered and concentrated in vacuo to give about 5 g crude product. Chromatographed through a pressure column eluting with 10% ethyl acetate-n-hexane to give 2.49 g of the title compound.

Step B: Preparation of 4H-2,3,5,6-tetrahydro-3-(2-methoxy)ethylthiopyran-4-one To a solution of 2.4 g (10.3 mmol) of product from Step A in 50 ml DMF was added 6 g (44.8 mmol) lithium iodide. The resulting solution was refluxed under $N_2$ for 2 hours. The reaction mixture was poured into 500 ml $H_2O$/HCl and extracted with ethyl acetate. THe organic solution was washed with water; saturated NaCl, dried over $MgSO_4$ and concentrated in vacuo to give 1.7 g crude product which was chromatographed through a pressure column eluting with 10% ethyl acetate/n-hexane to give 0.9 g of title compound.

Step C: Tetrahydro-3-(2-methoxyethyl)-4H-thiopyran-4-one-O-(2-hydroxy-3-((1-methylethyl)amino)propyl)oxime, ethanedioate (1:1 salt)

The title compound was prepared by the method described in Example 5, Step C, and has m.p. 99°–103° C. (as hydrogen oxalate salt).

Anal. Calc'd for $C_{14}H_{28}N_2O_3S \cdot C_2H_2O_4$: C, 48.71; H, 7.67; N, 7.10. Found: C, 48.63; H, 7.83; N, 7.20.

EXAMPLE 7

Dihydro-2,4-dimethyl-3(2H)-thiophenone-O-(2-hydroxy-3-((1-methylethyl)amino)propyl)oxime, ethanedioate (1:1 salt)

Employing the procedure substantially as described in Example 5, Step C, but using the 2,3,4,5-tetrahydro-2,4-dimethylthiophene-3-one prepared according to the procedures described in *J. Org. Chem.*, 48, 791 (1983) as starting material there was obtained the title compound with m.p. 85°–105° C.

Anal. Calc'd for $C_{12}H_{24}N_2O_2S_1 \cdot C_2H_2O_4$: C, 47.98; H, 7.48; N, 8.00. Found: C, 47.84; H, 7.71; N, 7.98.

EXAMPLE 8

Methyl tetrahydro-3-((2-hydroxy-3-((1-methylethyl)amino)-propoxy)imino-2 (and 4)-thiophenecarboxylate ethanedioate (2:1 salt)

A mixture of 1.60 g (10.0 mmol) 2-carbomethoxy-2,3,4,5-tetrahydro-3-thiophene and 4-carbomethoxy- 2,3,4,5-tetrahydro-3-thiophenone (5:1, purchased from Pfaltz and Bauer) was placed in 40 ml of ethanol. To this solution was added 2.32 g (10.5 mmol) of 3-(1-methylethylamino)-2-hydroxypropoxyamine dihydrochloride, 100 ml of water, and 1.72 g (21.0 mmol) of sodium acetate. The resulting solution was heated at reflux for two hours, cooled, and concentrated in vacuo. The residue was partitioned between saturated sodium bicarbonate solution (75 ml) and ethyl acetate (150 ml). The aqueous layer was extracted with ethyl acetate (75 ml). The combined extract was washed with brine, dried over sodium sulfate, filtered, and concentrated to give 2.00 g of an oil. The oil was flash chromatographed on silica gel, eluted with chloroform ammonia (saturated) to give 1.41 g (49%) of an inseparable mixture of the products in a 5:1 ratio as an oil.

To a solution of 1.36 g (4.7 mmol) of the mixture in ether (20 ml) was added a warm solution of 0.30 g (2.4 mmol) oxalic acid dihydrate in warm isopropanol (2 ml) to give a gum. The mixture was stirred, the supernatant was decanted, and the gum was washed with ether (20 ml) and dried in vacuo to give 1.0 g (68%) of the hemioxalate salt, m.p. 62°–71° C.

Anal. Calc'd for $C_{12}H_{22}N_2O_4S \cdot 0.5C_2H_2O_4 \cdot 0.75H_2O \cdot 0.1C_4H_{10}O$: C, 45.16; H, 7.21; N, 7.86. Found: C, 45.08; H, 7.32; N, 7.73.

EXAMPLE 9

Dihydro-2,4-dimethyl-2H-thiopyran-3(4H)-one-0-(2-hydroxy-3-((1-methylethyl)amino)propyl)oxime, ethanedioate (1:1 salt)

Employing the procedure substantially as described in Example 5, Step C, but using 2H,6H,-4,5-dihydro-2,4-dimethylthiopyran-3-one prepared according to the procedures described in *J. Org. Chem.*, 48, 791 (1983) as starting material there is obtained the title compound with m.p. 130°–133° C.

Anal. Calc'd for $C_{13}H_{26}N_2O_5S \cdot C_2H_2O_4$: C, 49.43; H, 7.74; N, 7.69. Found: C, 49.63; H, 7.98; N, 7.82.

EXAMPLE 10

Dihydro-2-(methoxymethyl)-3(2H)-thiophenone-0-(2-hydroxy-3-((1-methylethyl)amino)propyl)oxime, ethanedioate (1:1 salt)

Step A: Preparation of Methyl 1,4-dioxa-7-thiaspiro [4,4]nonane-6-carboxylate

A solution of 1.60 g (10.0 mmol) of 2-carbomethoxy-2,3,4,5-tetrahydrothiophen-3-one (contained 15% of the 4-carbomethoxy isomer, Pfaltz and Bauer), 1.4 g (24.0 mmol) of ethylene glycol, and 0.02 g of p-toluenesulfonic acid dihydrate in 20 ml of benzene was heated at reflux in a flask equipped with a Dean-Stark trap for 40 hours. The cooled solution was washed with saturated sodium bicarbonate solution (10 ml), water (3×5 ml), and brine, dried over sodium sulfate, filtered, and concentrated in vacuo to give 1.48 g of an oil. The oil was flash chromatographed on silica gel eluting with hexane:ether (3:1) to give 1.23 g (60%) product as an oil, a 5:1 mixture of the 6-carboxylate: 4-carboxylate; NMR (deuteriochloroform): δ 4.0 (m, 3H), 3.75 (S, 3H), 2.95 (m, 2H), 2.60 (d of d, 1H), 2.05 (d of d, 1H).

Step B: Preparation of 6-hydroxymethyl-1,4-dioxa-7-thiaspiro[4,4]nonane

To a suspension of 0.20 g (5.0 mmol) of 95% lithium aluminum hydride in 25 ml ether under argon cooled to 0° C. was added dropwise a solution of 1.12 g (5.5 mmol) of product from step A in 15 ml ether. The mixture was stirred at 0° C. for one hour. The reaction was quenched by dropwise addition of saturated sodium sulfate solution. The mixture was dried over sodium sulfate, filtered, and concentrated to give 0.87 g of an oil. The oil was flash chromatographed on silica gel eluting with chloroform to give 0.69 g (71%) of product as an oil; NMR (deuteriochloroform): δ 4.0 (m, 4H), 3.7 (m, 1H), 3.6 (m, 1H), 3.3 (m, 1H), 2,8 (m, 3H), 2.1 (m, 1H), 2.0 (m, 1H).

Step C: Preparation of 6-methoxymethyl-1,4-dioxa-7-thiaspiro[4,4]nonane

To a solution of 0.18 g (1.0 mmol) of compound from Step B, in 2 ml, dry, distilled THF under argon cooled to 0° C. was added dropwise 0.044 g (1.1 mmol) of 60% sodium hydride in mineral oil. The mixture was stirred for 30 minutes at 0° C. and a solution of 0.17 g (1.2 mmol) of methyl iodide in 1 ml THF was added dropwise. The mixture was stirred for 48 hours at room temperature. The reaction was quenched by addition of saturated sodium bicarbonate solution (2 ml) and water (1 ml), diluted with ether (15 ml) and the layers were separated. The ether layer was washed with brine, dried, filtered, and concentrated to give 0.17 g (89%) of product as an oil; NMR (deuteriochloroform): δ 4.0 (m, 4H), 3.65 (m, 1H), 3.41 (t, 2H), 3.36 (S, 3H), 2.81 (t, 2H), 2.1 (m, 2H).

Step D: Preparation of 2-methoxymethyl-2,3,4,5-tetrahydro-3-thiophenone

A solution of 0.16 g (0.84 mmol) of compound from Step C, 3.2 ml THF, 3.2 ml H$_2$O, and 4.8 ml acetic acid was heated at 70° C. for 48 hours. The cooled mixture was concentrated and the residue was dissolved in ethyl acetate, (50 ml) washed with saturated sodium bicarbonate solution (10 ml) and brine, dried, filtered, and concentrated to give 0.14 g of an oil. The oil was flash chromatographed on silica gel eluting with hexane:ether (3:1) to give 0.090 g (75%) product as an oil; NMR (deuteriochloroform): δ 3.7 (m, 2H), 3.5 (m, 1H), 3.37 (S, 3H), 2.05 (m, 1H), 1.95 (m, 1H), 2.65 (t, 2H).

Step E: Preparation of Dihydro-2-(methoxymethyl)-3(2H)-thiophenone-0-(2-hydroxy-3-((1-methylethyl)amino)propyl)oxime, ethanedioate (1:1 salt)

This compound was prepared in 73% yield by the procedure of Example 5, Step C, starting from 0.18 g (1.2 mmol) of compound from Step D, 0.28 g (1.3 mmol) of 3-(1-methylethylamino)-2-hydroxypropoxyimino hydrochloride, and 0.21 g (2.5 mmol) of sodium acetate in 4.8 ml ethanol and 12 ml water.

The product was isolated as the oxalate salt, m.p. 101°–118° C.

Anal. Calc'd for $C_{12}H_{24}N_2O_3S \cdot C_2H_2O_4$: C, 45.89; H, 7.15; N, 7.64. Found: C, 46.21; H, 7.45; N, 7.95.

EXAMPLE 11

4-((Acetyloxy)methyl)dihydro-4-methyl-3(2H)-thiophenone-0-(2-hydroxy-3-((1-methylethyl)-amino)-propyl)oxime, ethanedioate (2:1 salt)

Step A: Preparation of 4-Carbomethoxy-4-methyltetrahydrothiophenone

To a solution of 4.65 g (29.0 mmol) of 4-carbomethoxytetrahydro-3-thiophenone in 20 ml of dry DMSO cooled in a cold-water bath at 12° C. under argon was added 1.73 g (32.0 mmol) of sodium methoxide. The mixture was stirred 30 minutes and a solution of 4.97 g (35.0 mmol) of methyl iodide in 1 ml of dry DMSO was added dropwise. The mixture was stirred overnight at room temperature, than diluted with water (60 ml) and extracted with methylene chloride (3×75 ml). The extract was washed with water (50 ml) and brine, dried over sodium sulfate, filtered, and concentrated in vacuo to give 5.4 g of an oil. The oil was flash chromatographed on silica gel eluting with 3:1 hexane:ether to give 1.49 g (30%) of the product as an oil; NMR (deuteriochloroform): δ 3.76 (S, 3H), 3.70 (m, 1H), 3.50 (dd, 1H), 3.30 (dd, 1H), 2.83 (d, 1H), 1.46 (S, 3H).

Step B: Preparation of Methyl 9-methyl-1,4-dioxa-7-thiaspiro[4.4]-nonane-9-carboxylate A solution of 1.48 g (8.5 mmol) of product from Step A, 1.06 g (17.0 mmol) of ethylene glycol, and 0.02 g of p-toluenesulfonic acid dihydrate in 30 ml of benzene was heated at reflux in a flask equipped with a Dean-Stark trap for 48 hours. The cooled solution was washed with saturated sodium bicarbonate solution (15 ml), water (3×5 ml) and brine, dried and concentrated to give 1.59 g of an oil. The oil was flash chromatographed on silica gel eluting with 3:1 hexane:ether to give 0.99 g (53%) of the product as an oil. NMR: (deuteriochloroform): δ 4.0 (m, 4H), 3.72 (S, 3H), 3.52 (d, 1H), 2.93 (d of d, 2H), 2.71 (d, 1H), 1.44 (S, 3H).

Step C: Preparation of 9-hydroxymethyl-9-methyl-1,4-dioxa-7-thiaspiro[4.4-]nonane To a suspension of 0.18 g (4.5 mmol) of 95% lithium aluminum hydride in 24 ml of ether cooled to 0° C. under argon was added dropwise a solution of 0.98 g (4.5 mmol) of product from Step B in 16 ml of ether. The reaction mixture was stirred 1 hour at 0° C., than quenched by the dropwise addition of saturated sodium sulfate solution, dried over sodium sulfate, filtered, and concentrated to give 0.86 g (100%) of the product as an oil; NMR (deuteriochloroform): δ 4.0 (m, 4H), 3.62 (m, 2H), 3.02 (d, 1H), 2.88 (S, 2H), 2.63 (d, 1H), 2.60 (t, 1H, —OH), 1.12 (S, 3H).

Step D: Preparation of 4-Hydroxymethyl-4-methyltetrahydro-3-thiophenone

A solution of 0.23 g (1.2 mmol) of product from Step C, 4.8 ml THF, 4.8 ml H$_2$O, and 7.2 ml acetic acid was heated at 70° C. for 96 hours. The cooled mixture was concentrated and the residue was dissolved in ethyl acetate (75 ml), washed with saturated sodium bicarbonate solution (15 ml), and brine, dried, filtered, and concentrated to give 0.19 g of an oil. The oil was flash chromatographed on silica gel eluting with chloroform to give 0.09 g (50%) of product as an oil; NMR (deuteriochloroform): δ 3.79 (dd, 1H), 3.58 (dd, 1H), 3.33 (d, 2H), 3.30 (d, 1H), 2.71 (d, 1H), 1.98 (t, 1H, —OH), 1.22 (S, 3H).

Step E: Preparation of 4-methyl-3-oxo-tetrahydrothien-4-yl-methyl acetate

To a solution of 0.09 g (0.6 mmol) of compound from Step D, 0.071 g (0.70 mmol) of triethylamine and 5 mg of 4-dimethylaminopyridine in 1.5 ml of methylene chloride cooled to 0° C. under argon was added a solution of 0.055 g (0.70 mmol) of acetyl chloride in 0.5 ml of methylene chloride. The mixture was stirred for 3 hours at 0° C., diluted with 13 ml of methylene chloride, washed with saturated sodium bicarbonate solution; water (3 ml), and brine, dried, filtered, and concentrated to give 0.11 g (100%) of product; NMR (deuteriochloroform): δ 4.14 (d, 2H), 3.34 (S, 2H), 3.09 (d, 1H), 2.74 (d, 1H), 2.05 (S, 3H), 1.24 (S, 3H).

Step F: Preparation of 4-((Acetyloxy)methyl)dihydro-4-methyl-3(2H)-thiophenone-0-(2-hydroxy-3-((1-methylethyl)-amino)-propyl)oxime, ethanedioate (2:1 salt)

To a solution of 0.67 g (3.6 mmol) of compound from Step E in 14.4 ml ethanol was added 0.84 g (3.8 mmol) of 3-(1-methylethylamino)-2-hydroxypropoxyamine dihydrochloride, 36 ml of water and 0.62 g (7.6 mmol) of sodium acetate. The reaction was carried out as in previous Example 5, Step C, to give 0.93 g crude product. The crude product was flash chromatographed on silica gel eluting with 2% methanol/chloroform/ammonia to give 0.64 g (56%) of the product.

The product was isolated as the hemioxalate hemihydrate salt, m.p. 41°–47° C.

Anal. Calc'd for: $C_{14}H_{26}N_2O_4S.0.5C_2H_2O_4.0.5H_2O$: C, 48.37; H, 7.58; N, 7.52. Found: C, 48.28; H, 7.65; N, 7.44.

EXAMPLE 12

Dihydrothieno[2,3-b]thiopyran-4-one-0-((S)-2-hydroxy-3-((1,1-dimethylethyl)amino)propyl)oxime, hydrochloride

Step A: Preparation of 5,6-dihydro-4-hydroximinothieno[2,3-b]thiopyran

To a solution of 5,6-dihydrothieno[2,3-b]thiopyran-4-one (5.0 g, 29.4 mmol) in ethanol (98 ml) was added a solution of hydroxylamine hydrochloride (4.9 g, 70.6 mmol) in 2:1 water-ethanol (27 ml). Sodium acetate.3-H$_2$O (9.6 g, 70.6 mmol) in 2:1 water-ethanol (27 ml) was added and the solution was heated at reflux for 2 hours. The reaction mixture was concentrated to dryness, water was added and the solid product (5.3 g, 98%) was collected and dried. An analytical sample was prepared by recrystallization from acetonitrile; m.p. 123°–124° C.

Anal. Calc'd for $C_7H_7NOS_2$: C, 45.38; H, 3.82; N, 7.56. Found: C, 45.67; H, 3.81; N, 7.47.

Step B: Preparation of Dihydrothieno[2,3-b]thiopyran-4-one-0-((S)-2-hydroxy-3-((1,1-dimethylethyl)amino)propyl)oxime, hydrochloride A solution of product from Step A (2.4 g, 13.0 mmol) and NaH (0.6 g, 60% in mineral oil, 15.4 mmol) in DMF (26 ml) was heated to 60° C. A solution of (S)-2-phenyl-3-t-butyl-5-toluenesulfonyloxymethyloxazolidine (5.6 g, 14.3 mmol), prepared from 2-phenyl-3-tert-butyl-5-(hydroxymethyl)oxazolidine, in DMF (10 ml) was added dropwise and the resulting solution was heated at 100° C. for 18 hours. The solution was poured into water (100 ml), extracted with ethyl acetate, and the organic layers were washed with water and brine, dried and concentrated. To a solution of the residue in water (100 ml) was added concentrated acetic acid (10 ml). After stirring at room temperature overnight, the solution was extracted with ether. The aqueous phase was made basic with saturated sodium carbonate and extracted with chloroform. The organic layers were dried and concentrated to give an oil which was chromatographed (silica gel, methanol-chloroform-ammonia, 5%). Hydrogen chloride ethanol (2.55N) was added to the residue and the resulting solid was recrystallized in isopropanol to give the title compound (1.8 g, 44%); m.p. 171°–173° C.

Anal. Calc'd for $C_{14}H_{23}ClN_2O_2S_2$: C, 47.91; H, 6.62; N, 7.98. Found: C, 48.02; H, 6.73; N, 7.99.

Employing the procedures substantially as described in Example 12, but starting with the appropriate thiopyran there are also prepared:

Dihydrothieno[2,3-b]thiopyran-4-one-0-((R)-2-hydroxy-3-((1,1-dimethylethyl)amino)propyl)oxime hydrochloride;

Dihydrothieno[2,3-b]thiopyran-4-one-7,7-dioxide-0-((R,S)-2-hydroxy-3-((1,1-dimethylethyl)amino)-propyl)oxime, m.p. 80°–90° C.;

Dihydrothieno]2,3-b]thiopyran-4-one-7,7-dioxide-0-((R)-2-hydroxy-3-((1,1-dimethylethyl)amino)propyl-)oxime;

Dihydrothieno[2,3-b]thiopyran-4-one-0-((R,S)-2-hydroxy-3-((1-methylethyl)amino)propyl)oxime, hydrochloride, m.p. 132°–134° C.;

Dihydrothieno[2,3-b]thiopyran-4-one-7,7-dioxide-0-((S)-2-hydroxy-3-((1,1-dimethylethyl)amino)propyl-)oxime

EXAMPLE 13

| | | |
|---|---|---|
| Tetrahydro-4H—thiopyran-4-one-0-(3-((1,1-dimethyl-ethyl)-amino-)-2-hydroxypropyl)oxime monohydrochloride | 1 mg | 15 mg |
| Monobasic sodium phosphate 2H₂O | 9.38 mg | 6.10 mg |
| Dibasic sodium phosphate .12H₂O | 28.48 mg | 16.80 mg |
| Benzalkonium chloride | 0.10 mg | 0.10 mg |
| Water for injection q.s. ad. | 1.0 ml | 1.0 ml |

The novel compound, phosphate buffer salts, and benzalkonium chloride are added to and dissolved in water. The pH of the composition in adjusted to 6.8 and diluted to volume. The composition is rendered sterile by ionizing radiation.

EXAMPLE 14

| | |
|---|---|
| Tetrahydro-3-methyl-4H—thiopyran-4-one-0-(2-hydroxy-3-((1-methyl-ethyl)amino)propyl)oxime, monohydrochloride | 5 mg |
| petrolatum q.s. ad. | 1 gram |

The compound and the petrolatum are aseptically combined.

EXAMPLE 15

| | |
|---|---|
| Tetrahydro-3-methyl-4H—thiopyran-4-one-0-(2-hydroxy-3-((1-methyl-ethyl)amino)propyl)oxime, monohydrochloride | 1 mg |
| Hydroxypropylcellulose q.s. | 12 mg |

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

What is claimed is:

1. A compound of structural formula:

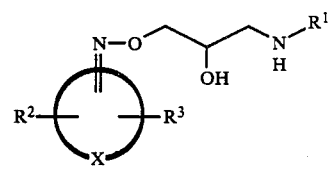

or a pharmacologically acceptable salt thereof wherein
X is —S—, or —S(CH₂)₂S—;
$R^1$ is $C_{1-6}$ alkyl, or phenyl-$C_{1-6}$alkyl; and
$R^2$ and $R^3$ are independently
(a) hydrogen,
(b) $C_{1-6}$ alkyl, either unsubstituted or substituted with —OH, —COR¹ or COAr or OCOR¹, or
(c) —COOR¹:

represents a saturated ring of from 5 to 8 members.

2. The compound of claim 1, wherein

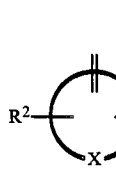 is

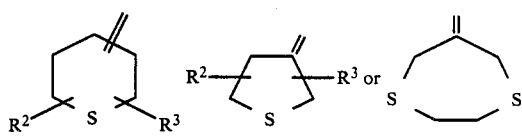

wherein $R^2$ and $R^3$ are independently hydrogen or $C_{1-2}$alkyl either unsubstituted or substituted with —OCH₃, or —OCOCH₃, and $R^1$ is t-butyl or isopropyl.

3. The compound of claim 2 of structural formulae:

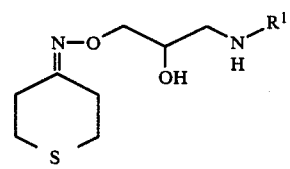

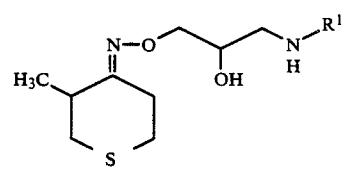

-continued

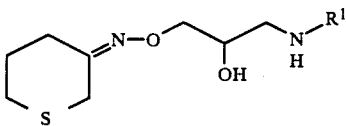

4. A pharmaceutical formulation for the treatment of hypertension, angina, or arrhythmia which comprises a pharmaceutical carrier and an effective amount of the compound of claim 1.

5. An ophthalmological formulation for the treatment of ocular hypertension and glaucoma which comprises a pharmaceutical carrier and an effective ocular antihypertensive and antiglaucomatous amount of the compound of claim 2.

6. A method of treating hypertension, angina, or arrhythmia which comprises the administration to a patient in need of such treatment of an effective amount of the compound of claim 1.

7. A method of treating occular hypertension and glaucoma which comprises the topical ocular administration to a patient in need of such treatment of an effective ocular antihypertensive amount of the compound of claim 2.

* * * * *

UNITED STATES PATENT AND TRADEMARK OFFICE
CERTIFICATE OF CORRECTION

PATENT NO. : 4,803,286
DATED : February 7, 1989
INVENTOR(S) : Baldwin et al

It is certified that error appears in the above-identified patent and that said Letters Patent is hereby corrected as shown below:

In the Title, change "α-Blockers" to --β-Blockers--.

Signed and Sealed this

Twenty-fifth Day of July, 1989

Attest:

DONALD J. QUIGG

Attesting Officer

Commissioner of Patents and Trademarks